United States Patent [19]

Semeraro et al.

[11] Patent Number: 5,091,395
[45] Date of Patent: * Feb. 25, 1992

[54] HETEROCYCLIC COMPOUNDS AND THEIR PHARMACEUTICAL FORMULATION

[75] Inventors: Claudio Semeraro, Bresso; Dino Micheli, Modena; Daniele Pieraccioli; Giovanni Gaviraghi, both of Verona, all of Italy; Alan D. Borthwick, London, England

[73] Assignee: Glaxo S.p.A., Verona, Italy

[*] Notice: The portion of the term of this patent subsequent to Jan. 31, 2006 has been disclaimed.

[21] Appl. No.: 270,487

[22] Filed: Nov. 4, 1988

Related U.S. Application Data

[63] Continuation of Ser. No. 897,351, Aug. 18, 1986, abandoned.

[30] Foreign Application Priority Data

Aug. 21, 1985 [IT]  Italy .................. 21959 A/85
Feb. 20, 1986 [IT]  Italy .................. 19479 A/86

[51] Int. Cl.$^5$ .................. C07D 211/86; A61K 31/455
[52] U.S. Cl. .................. 514/356; 546/321
[58] Field of Search .................. 546/321; 514/356

[56] References Cited

U.S. PATENT DOCUMENTS

| | | | |
|---|---|---|---|
| 3,923,818 | 12/1975 | Bossert et al. | 546/321 |
| 4,145,432 | 3/1979 | Sato | 514/356 |
| 4,307,103 | 12/1981 | Sato et al. | 546/321 |
| 4,430,333 | 2/1984 | Campbell et al. | 546/321 |
| 4,492,703 | 1/1985 | Goldmann et al. | 546/321 |
| 4,801,599 | 1/1989 | Semeraro et al. | 546/321 |

OTHER PUBLICATIONS

Ca 93:204462g. Teraji et al.

Rahwan et al., Annual Reports in Medicinal Chemistry 1981, pp. 257-264.
Thomas, G. et al., J. Cardiovascular Pharm. 6, pp. 1170-1176, (1984).

*Primary Examiner*—Jane T. Fan
*Attorney, Agent, or Firm*—Morgan & Finnegan

[57] ABSTRACT

Compounds are described of the formula

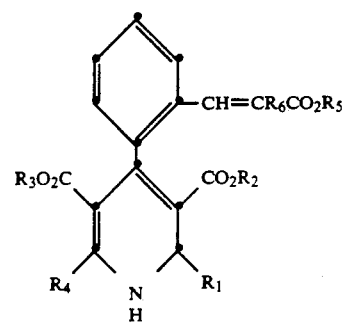

(I)

wherein
$R_1$ and $R_4$ independently represent a $C_{1-4}$ alkyl group;
$R_2$ and $R_3$ independently represent a $C_{1-6}$ straight or branched alkyl chain or alkoxy group;
$R_5$ represents a straight or branched chain $C_{1-13}$ alkyl group or a $C_{5-8}$ cycloalkyl group which may be substituted by a $C_{1-3}$ alkyl substituent;
$R_6$ represents a halogen atom or a straight or branched $C_{1-3}$ alkyl group.

The compounds represented by formula (I) reduce intracellular calcium ion concentration by limiting transmembranal calcium ion reflux and thus may be useful for the treatment of cardiovascular disorders such as hypertension.

18 Claims, No Drawings

HETEROCYCLIC COMPOUNDS AND THEIR PHARMACEUTICAL FORMULATION

This application is a continuation of Ser. No. 897,351, filed Aug. 18, 1986, now abandoned.

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. Furthermore it has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heart failure, cerebral vascular and peripheral disorders.

The invention thus provides compounds of the general formula (I).

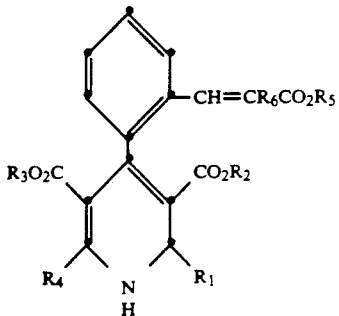

wherein
$R_1$ and $R_4$ independently represent a $C_{1-4}$ alkyl group;
$R_2$ and $R_3$ independently represent a $C_{1-6}$ straight or branched chain alkyl or alkoxyalkyl group;
$R_5$ represents a $C_{1-13}$ straight or branched chain alkyl group or a $C_{5-8}$ cycloalkyl group which may be substituted by a $C_{1-3}$ alkyl group; and
$R_6$ represents a halogen atom or a straight or branched $C_{1-3}$ alkyl group.

The compounds represented by formula (I) can exist in more than one isomeric and/or enantiomeric form and the invention includes all such isomers, enantiomers and mixtures thereof.

Examples of suitable groups for $R_1$ and $R_4$ independently include methyl and ethyl groups.

Examples of suitable groups for $R_2$ and $R_3$ independently include $C_{1-4}$ straight or branched chain alkyl groups such as methyl, ethyl, isopropyl, isobutyl, t-butyl or $C_{1-3}$ alkyl (such as ethyl) substituted by a $C_{1-3}$ alkoxy (e.g. methoxy or propoxy) group.

When the group $R_5$ represents a $C_{1-13}$ alkyl group this may for example be a methyl, ethyl, propyl, isopropyl, butyl, sec butyl isobutyl, tert butyl, pentyl, isopentyl, neopentyl, hexyl, 2,6-dimethyl-4-heptyl, octyl or a tridecyl group. When $R_5$ represents a cycloalkyl group, conveniently this represents a cyclopentyl, cyclohexyl or cycloheptyl group, which may be substituted by a methyl group.

When the group $R_6$ represents a halogen atom this may be for example a chlorine, bromine or iodine atom.

When the group $R_6$ represents a $C_{1-3}$ alkyl group examples of suitable groups include methyl, ethyl and propyl groups.

The group $-CH=CR_6CO_2R_5$ in the compounds of formula (I) can exist in the cis or the trans configuration. Preferred compounds are those in which the hydrogen atom and the group $R_6$ are in the trans configuration with respect to each other and these isomers are referred to hereinafter as trans isomers.

Preferably $R_1$ and $R_4$ represent methyl groups.

$R_2$ and $R_3$ preferably independently represent $C_{1-4}$ alkyl e.g. methyl, ethyl, isopropyl or isobutyl or $C_{1-3}$ alkoxyethyl e.g. methoxyethyl or propoxyethyl groups.

$R_5$ preferably represents a $C_{2-9}$ straight or branched chain alkyl group such as an ethyl, propyl, secbutyl, tert butyl, pentyl or octyl group or a $C_{5-7}$ cycloalkyl group which may be substituted by a $C_{1-3}$ alkyl group e.g. cyclohexyl optionally substituted by methyl.

$R_6$ preferably represents bromine or more particularly methyl or ethyl.

A particularly preferred class of compounds of the invention are those of formula (I) wherein $R_1$ and $R_4$ represent methyl, $R_2$ and $R_3$ independently represent methyl, ethyl or isopropyl, $R_5$ represents $C_{2-9}$ alkyl, more particularly ethyl, propyl, secbutyl, tert butyl, pentyl, octyl or a cyclohexyl group and $R_6$ represents methyl or ethyl.

Within this particularly preferred class of compounds those where $R_1$ and $R_4$ represent methyl, $R_2$ and $R_3$ represent ethyl and $R_5$ represents cyclohexyl, pentyl, secbutyl or tertiary butyl are especially preferred.

A particularly preferred compound according to the invention is 4-(2-(3-(1,1-dimethylethoxy)-3-oxo-2-methyl-1-propenyl)phenyl)-1,4-dihydro-2,6-dimethyl-3,5-pyridinedicarboxylic acid diethyl ester and more especially the E isomer thereof.

Other preferred compounds according to the invention 4-(2-(3-(1-methylpropoxy)-3-oxo-2-methyl-1-propenyl)-phenyl)-1,4-dihydro-2,6-dimethyl-3,5-pyridinedicarboxylic acid diethyl ester;

4-(2-(3-(cyclohexyloxy)-3-oxo-2-methyl-1-propenyl)-phenyl)-1,4-dihydro-2,6-dimethyl-3,5-pyridinedicarboxylic acid diethyl ester;

4-(2-(3-ethoxy-3-oxo-2-ethyl-1-propenyl)phenyl)-1,4-dihydro-2,6-dimethyl-3,5-pyridinedicarboxylic acid diethyl ester;

and more particularly the E isomers thereof.

The ability of the compounds to limit or inhibit the effect of calcium ions on the tone of vascular smooth muscle was determined using a depolarised rabbit ear artery prepared according to the method of Towart. R. et al Br. J. Pharmacol. 1982, 75, 1508.

The antihypertensive activity of the compounds of the invention may be demonstrated by intravenous and-/or oral administration of the compound to male spontaneously hypertensive rats. In these tests compounds of the invention have been found to have a particularly advantageous profile of activity including a relatively long duration of action.

The compounds of the invention are thus of interest in the treatment of hypertension. They are also potentially useful for the treatment of other cardiovascular disorders such as angina pectoris, myocardial ischaemia, congestive heart failure, cerebral vascular and peripheral disorders.

The compounds of the invention may be formulated in a conventional manner for use with one or more pharmaceutical carriers or excipients.

Thus a further aspect of the invention includes pharmaceutical compositions the compounds of formula (I) formulated for oral, sub lingual, transdermal, parenteral or rectal administration.

For oral administration the pharmaceutical composition may take the form of for example tablets, which may be film or sugar coated, capsules, powders, granules, solutions including syrups, or suspensions prepared by conventional means with acceptable excipients. For sub lingual administration the composition may take the form of tablets or lozenges formulated in the conventional manner.

For parenteral administration the compounds of formula (I) may be given as a bolus injection or by continuous infusion. The compositions may take such forms as suspensions, solutions or emulsions in oily or aqueous vehicles and may contain formulatory agents such as suspending, stabilising and/or dispersing agents. For administration by injection these may take the form of an unit dose presentation or as a multidose presentation preferably with an added preservative. administration by injection these may take the form of an unit dose presentation or as a multidose presentation preferably with an added preservative.

Alternatively for parenteral administration the active ingredient may be in powder form for reconstitution with a suitable vehicle.

The compounds of formula (I) may be formulated as ointments and creams for transdermal administration and as suppositories or retention enemas for rectal administration.

A proposed daily dosage of active compound of the invention for the treatment of man is in the range of 0.01 mg to 20 mg, which may conveniently be administered in one or more doses. The precise dose employed will depend on the age and condition of the patient as well as the route of administration.

For oral use the compounds of the invention are conveniently administered to the human patient at a dose in the range 0.1 mg to 20 mg per day. For parenteral use the compounds of the invention are conveniently administered at a dose in the range of 0.01–0.5 mg per day.

For oral use the compound is preferably administered twice or more particularly once a day.

Methods for preparing the compounds of formula (I) are described below and for the intermediates described below $R_1$, $R_2$, $R_3$, $R_4$, $R_5$ and $R_6$ have the meanings defined above for compounds of formula (I) or are such groupings in a protected form.

Thus compounds of formula (I) and more particularly the trans isomers thereof, may be prepared by reaction the $\alpha,\beta$-unsaturated ketone (II) with the aminoester (III). The reaction is conveniently carried out in a solvent such as an alkanol, e.g. ethanol or isopropanol and preferably with heating e.g. 40°–150° C.

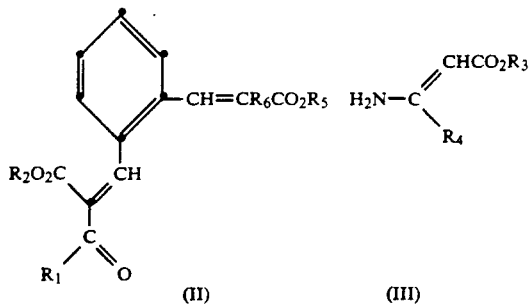

(II)    (III)

The $\alpha,\beta$-unsaturated ketone (II) may be prepared by reacting the aldehyde (IV) with the ketoester (V), in a solvent such as an alkanol e.g. ethanol or isopropanol, preferably with heating e.g. 40°–150° C. Conveniently this reaction is carried out in the presence of a catalyst such as piperidine acetate.

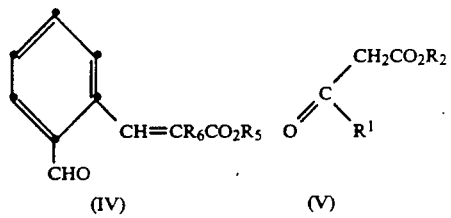

(IV)    (V)

In a modification of this process for preparing compounds of formula (I), the aldehyde (IV) may be reacted with a mixture of the aminoester (III) and the ketoester (V) under the conditions previously described for the reaction of the $\alpha,\beta$-unsaturated ketone (II) with the aminoester (III).

Compounds of formula (I) and in particular the trans isomers thereof in which $R_1$ and $R_4$ are the same and $R_2$ and $R_3$ are the same may be prepared by reacting the aldehyde (IV) with the aminoester (III) in the presence of a suitable acid catalyst. Examples of suitable acid catalysts include organic acids such as oxalic acid, alkanoic acids e.g. acetic acid or haloalkanoic acids such as trichloroacetic acid or trifluoroacetic acid or pyridinium salts thereof, or a sulphonic acid such as an alkanesulphonic acid e.g. methanesulphonic acid or an arylsulphonic acid e.g. benzenesulphonic acid or p-toluenesulphonic acid or a tetrahaloboric acid such as tetrafluoroboric acid. The reaction is preferably carried out in the presence of a solvent and at a temperature within the range of −70° to 30° C. preferably −30° to 10° C. Suitable solvents for the reaction include aprotic solvents such as hydrocarbons, e.g. hexane or cyclohexane, acetonitrile or ethers such as tertiary butyl methyl ether, dioxan or tetrahydrofuran, or protic solvents such as an alkanol e.g. methanol, ethanol, propanol, isopropanol or butanol.

Compounds of formula (I) and more particularly the trans isomers thereof in which $R_1$ and $R_4$ are the same and $R_2$ and $R_3$ are the same may also be prepared by reacting the aldehyde (IV) with the ketoester (V) and ammonium acetate. This reaction is conveniently carried out in a solvent such as pyridine with heating at 50°–120° C., conveniently at reflux.

In a further process of the invention compounds of formula (I) may be prepared by esterifying the corresponding acid of formula (I) in which $R_5$ is hydrogen.

Thus in one embodiment of this process compounds of formula (I) may be prepared by treating a compound of formula (I) in which $R_5$ is hydrogen with an alkylating agent $R_5X$ where $R_5$ is as defined in formula (I), and X is a leaving group such as chloride, bromide, iodide or mesylate. The reaction is preferably carried out in the presence of a base such as an alkali or alkaline earth metal carbonate e.g. potassium carbonate in a polar aprotic solvent such as dimethylformamide or dimethylsulphoxide optionally with heating. Thus for example the reaction may be carried out a temperature within the range 10°-100°.

The compounds of formula (I) wherein $R_5$ represents hydrogen may be prepared by hydrolysis of a compound of formula (I) wherein $R_5$ represents a tertiary butyl group. The hydrolysis may be carried out using hydrogen bromide in acetic acid, in the presence of a solvent such as dichloromethane. Preferably the reaction is carried out at low temperatures e.g. $-78°$-$35°$ C.

In yet another process of the invention the trans isomers of compounds of formula (I) wherein $R_6$ represents an alkyl group may be prepared by treating a compound of formula (VI)

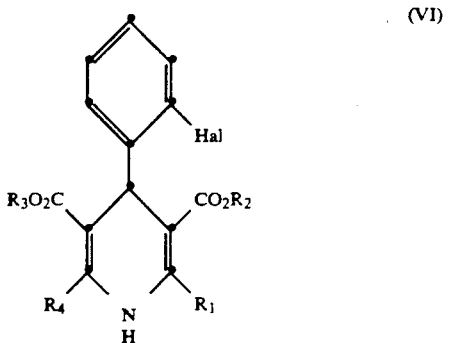

(VI)

(where Hal represents a bromine or iodine atom) with an acrylic ester $CH_2=CR_6CO_2R_5$ (VII) in which $R_6$ represents an alkyl group, in the presence of a catalytic amount of a palladium salt such as palladium acetate, in the presence of a suitable organic base such as a trialkylamine e.g. triethylamine or tri-n-butylamine. The reaction is also preferably carried out in the presence of a triarylphosphine such as tri-o-tolyphosphine, or more preferably, triphenylphosphine.

The reaction is conveniently carried out in a suitable solvent such as xylene or t-butyl acetate, or more conveniently in dimethylformamide or in a mixture of solvents e.g. xylene/dimethylformamide, preferably with heating. The reaction mixture is preferably heated within the temperature range of 80° C. to 150° C., more preferably at 100° C. to 110° C.

The carboxylic acids represented by the compounds of formula (I) wherein $R_5$ represents hydrogen are new compounds and useful chemical intermediates for preparing the compounds of formula (I) and represent a further feature of the invention.

Compounds of formula (IV) may be prepared by reacting the bis aldehyde (VIII) with the triphenylphosphorane (IX) in solvent such as methylene chloride or toluene.

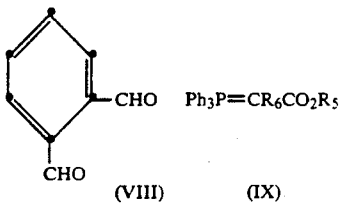

(VIII)    (IX)

Compounds of formula (IV) may also be prepared by reacting a 2-halobenzaldehyde (X)

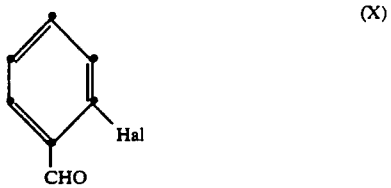

(X)

(where Hal represents a bromine or iodine atom) with an acrylic ester (VII). The reaction takes place under the conditions previously described for the reaction between the compound of formula (VI) and the acrylic ester (VII).

The compounds of formula (VI) may be prepared by reacting the 2-halobenzaldehyde (X) with the aminoester (III) and/or the ketoester (V) according to the conditions described above for the reaction between the compound of formula (IV) and the aminoester (III) and/or the ketoester (V).

The compounds of formulae (III), (V), (VII), (VIII), (IX) and (X) are either known compounds or may be made by analogous processes to those used for known compounds.

Compounds of formula (I) in which the group $-CH=CR_6CO_2R_5$ is in the cis configuration may be prepared by irradiating a solution of the corresponding trans isomer. Thus when a solution of the trans isomer in dichloromethane under a atmosphere of nitrogen is exposed to daylight a mixture of the cis and trans isomers are obtained and these may be separated by standard techniques such as fractional crystallisation and/or chromatography.

Compounds of formula (I) may also be prepared from the reaction of the compound (XI) with the phosphorane (IX) in a suitable solvent such as dichloromethane, tetrahydrofuran or toluene. Preferably the reaction is carried out with heating for example 40°-120° C., conveniently at reflux.

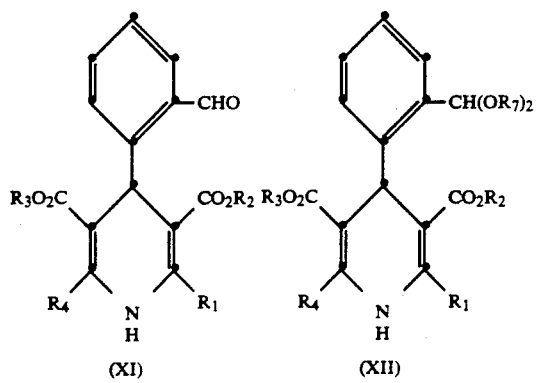

(XI)    (XII)

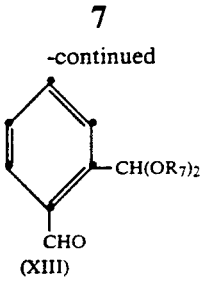

(XIII)

The intermediate (XI) may be prepared by aqueous acid hydrolysis of the corresponding acetal (XII; in which R$_7$ represents an alkyl group)

The compound of formula (XII) may be prepared from the aldehyde (XIII) by reaction with a compound of formula (III) and/or (V) under the conditions described above for preparing compounds of formula (I) from the intermediate (IV). The intermediate (XIII) may be prepared from the bromobenzene derivative (XIV) by reaction with butyl lithium in solvent followed by addition of dimethylformamide.

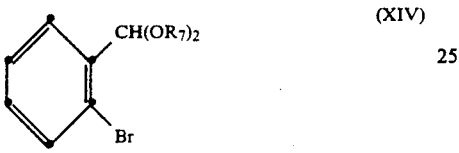

(XIV)

The following examples illustrate the invention. Temperatures are in °C. Throughout the examples reference to t.l.c. means thin layer chromatography on silica plates.

INTERMEDIATE 1

(a) (E)-3-(2-Formylphenyl)-2-methyl-2-propenoic acid ethyl ester

A solution of 2-(triphenylphosphoranilidene)-propanoic acid ethyl ester (8 g) in dry dichloromethane was added to a solution of ortho phtalaldehyde (2.9 g) in dry dichloromethane (10 ml) at 0° C. The solvent was evaporated and the oil taken up with diethyl ether. The solid triphenylphosphine oxide was filtered, washed with ether and the solution evaporated to dryness to give a colourless oil which was eluted on a silica gel column (diethyl ether/petrol ether, 1:1) to give the title compound as a colourless oil (4.3 g).

Similarly prepared was:

(b) (E)-3-(2-Formylphenyl)-2-methyl-2-propenoic acid 1,1-dimethyl ethyl ester

From 2-(triphenylphosphoranylidene)propanoic acid 1,1-dimethyl ethyl ester and ortho phtalaldehyde (c) (E)-3-(2-Formylphenyl)-2-ethyl-2-propenoic acid ethyl ester A solution of 2-(triphenylphosphoranylidene)-butanoic acid ethyl ester (5.6 g) in dry chloromethane (10 ml) was added to a solution of ortho phthalaldehyde (2 g) in dry dichloromethane (10 ml) at 0° C. The solvent was evaporated and the oil taken up with diethyl ether. The solid triphenylphosphine oxide was filtered, washed with ether and the solution evaporated to dryness to give a colourless oil which was eluted on a silica gell column (gradient Petrol ether/ethyl acetate, 9:1–8:2) to give the title compound as a colourless oil (3 g).

Similarly prepared was:

(d) (E)-3-(Formylphenyl)-2-ethyl-2-propenoic acid 1,1-dimethylethyl ester from o-phthalaldehyde and 2-(triphenylphosphoranilydene) butenoic acid 1,1-dimethylethyl ester (e) (E)-3-(2-Formylphenyl)-2-propyl 2-propenoic acid ethyl ester as a colourless oil was prepared from o-phthalaldehyde and 2-(triphenylphosphoranylidene)-pentanoic acid ethyl ester.

INTERMEDIATE 2

3-(2-Formylphenyl)-2-bromo-2-propenoic acid, diethyl ester

A solution of 2-bromo-2-(triphenylphosphoranylidene)acetic acid, ethyl ester (15 g) in dry dichloromethane (30 ml) was added to a solution of orthophthalaldehyde (4.7 g) in dry dichloromethane (30 ml), at 0° C. The solvent was evaporated and the oil taken up with diethyl ether. The solid triphenylphosphine oxide was filtered, washed with ether and the solution evaporated to dryness to give a colourless oil which was eluted on a silica gel column (gradient petrol ether/ethyl acetate, 8:2→6:4) to give the title compound (6.2 g) as a colourless oil (6.2 g). T.l.c. (Petrol ether/ethyl acetate, 7:3) Rf 0.41.

EXAMPLE 1

(a) (E)-4-(2-(3-Ethoxy-3-oxo-2-methyl-1-propenyl)-phenyl)-1,4-dihydro-2,6-dimethyl-3,5-pyridinedicarboxylic acid diethyl ester 3-Amino-2-butenoic acid ethyl ester was dissolved in acetic acid (3 ml) and treated with a solution of Intermediate 1(a) (3 g) in acetic acid (5 ml) at room temperature. The solution was stirred at room temperature for 2 h then poured into water and extracted with ethyl acetate. The organic phase was washed with 5% NaHCO$_3$ then with water and dried over Na$_2$SO$_4$. Evaporation of the solvent gave a yellow oil which was eluted twice on a silica gel column (Petrol ether/ethyl acetate, 7:3) to give a yellow solid. This was recrystallized from petrol ether/diethyl ether (1:1) to give the title compound as a pale yellow solid (0.45 g). M.p. 105°–106°.

Microanalysis for C$_{25}$H$_{31}$NO$_6$ Requires C 68.00; H 7.08; N 3.17; Found: C 67.68; H 7.09; N 3.15%.

Similarly prepared was:

(b) (E)-4-(2-(3-(1,1-Dimethylethoxy)-3-oxo-2-methyl-1-propenyl)phenyl)-1,4-dihydro-2,6-dimethyl-3,5-pyridinedicarboxylic acid diethyl ester M.p. 130°–131°

From (E)-3-(2-Formylphenyl)-2-methyl-2-propenoic acid 1,1-dimethyl ethyl ester and Intermediate 1(b)) and 3-amino-2-butenoic acid ethyl ester.

Microanalysis for C$_{27}$H$_{35}$NO$_6$ Requires C 69.0; H 7.5; N 3.0; Found: C 69.1; H 7.5; N 3.0%.

(c) (E)-4-(2-(3-Ethoxy-3-oxo-2-ethyl-1-propenyl)-phenyl)-1,4-dihydro-2,6-dimethyl-3,5-pyridinedicarboxylic acid diethyl ester A solution of Intermediate 1(c) (6 g) in ethanol (50 ml) was cooled to −10° C. and then trifluoroacetic acid (4 ml) was added followed by a solution of 3-amino-2-butanoic acid ethyl ester (17 g) in ethanol (50 ml). The mixture was stirred at −10° C. for 1 hr, evaporated in vacuo and the residue taken up in ethyl acetate, washed with 10% HCl (3×50 ml), then with water and dried over Na$_2$SO$_4$. Evaporation of the solvent gave an oil which was purified by column chromatography on silica (Petrol ether/diethyl ether, gradient 7:3–3:7) to give the title compound as a white solid. M.p. 92°–94°.

Microanalysis for C$_{26}$H$_{33}$NO$_6$ Requires C 68.56; H 7.30; N 3.07; Found: C 68.72; H 7.33; N 3.08%.

Similarly prepared were:

(d) (E)-4-(2-(3-Ethoxy-3-oxo-2-propyl-1-propenyl)-phenyl)-1,4-dihydro-2,6-dimethyl-3,5-pyridinedicarboxylic acid diethyl ester M.p. 93°–95°

Microanalysis for $C_{27}H_{35}NO_6$ Requires C 69.06; H 7.51; N 2.98; Found: C 69.13; H 7.52; N 2.98%.

From Intermediate (1e) and 3-amino-2-butenoic acid ethyl ester.

(e) E-4-(2-(3-(1,1-dimethylethoxy-3-oxo-2-ethyl-1-propenyl)phenyl)-1,4-dihydro-2,6-dimethyl-3,5-pyridine dicarboxylic acid diethyl ester m.p. 99°–101° C.

T.l.c. (Ethyl ether/petrol 1:1) Rf 0.54 from Intermediate (1d) and 3-amino-2-butenoic acid ethyl ester.

EXAMPLE 2

(a) (E)-4-(2-(3-Ethoxy-3-oxo-2-methyl-1-propenyl)-phenyl)-1,4-dihydro-2,6-dimethyl-3,5-pyridinedicarboxylic acid diethyl ester (i) (E)-4-(2-(2-Carboxy-1-propenyl)phenyl)-1,4-dihydro-2,6-dimethyl-3,5-pyridinedicarboxylic acid diethyl ester (Compound A)

To a solution of (E)-4-(2-(3-(1,1-Dimethylethoxy)-3-oxo-2-methyl-1-propenyl)phenyl-1,4-dihydro-2,6-dimethyl-3,5-pyridinedicarboxylic acid diethyl ester, (Example 1b) (5 g) in dichloromethane (30 ml) at −38° was added to a solution of 33% acetic acid/HBr (15 ml) in dichloromethane (30 ml) slowly. The mixture was then warmed to −30° and stirred at −30° C. for 20 minutes. The mixture was poured into ice water, NaHCO$_3$ (5 g) was added and the mixture was extracted with dichloromethane, washed with water and dried over Na$_2$SO$_4$. Evaporation of the solvent gave a solid which was recrystallized from petrol ether/ethyl acetate (1:1) to give the title compound as a white solid (3.5 g). M.p. 205°–207°.

In a similar manner E-4-(2-(2-Carboxy-1-butenyl)-phenyl)-1,4-dihydro-2,6-dimethyl-3,5-pyridinedicarboxylic acid diethylester (Compound B) m.p. 191°–193° was prepared from the compound of Example 1e.

(ii) (E)-4-(2-(3-Ethoxy-3-oxo-2-methyl-1-propenyl)-phenyl)-1,4-dihydro-2,6-dimethyl-3,5-pyridinedicarboxylic acid diethyl ester A suspension of Compound A (4 g), ethyl bromide (1 g) and potassium carbonate (30 g) in dimethylformamide (60 ml) was stirred at room temperature for 6 h. The mixture was poured into water and extracted with ethyl acetate, then washed thoroughly with water and dried over Na$_2$SO$_4$. Evaporation of the solvent gave an oil which was triturated with petrol and recrystallized from petrol ether to give the title compound as a white solid (3.2 g). M.p. 105°–106°.

T.l.c. (Petrol ether/ethyl acetate, 1:1) Rf. 0.40.

Similarly prepared were:

2(b) (E)-4-(2-(3-Cyclohexyloxy-3-oxo-2-methyl-1-propenyl)phenyl)-1,4-dihydro-2,6-dimethyl-3,5-pyridinedicarboxylic acid diethyl ester M.p. 131°–132°.

Microanalysis for $C_{29}H_{37}NO_6$ Requires C 70.3; H 7.5; N 2.8; Found: C 70.4; H 7.7; N 2.7%.

From Compound A and cyclohexyl bromide stirring for 20 h at 40°.

2(c) (E)-4-(2-(3-Propoxy-3-oxo-2-methyl-1-propenyl)phenyl)-1,4-dihydro-2,6-dimethyl-3,5-pyridinedicarboxylic acid diethyl ester M.p. 108°–110° C.

Microanalysis for $C_{26}H_{33}NO_6$ Requires C 68.55; H 7.30; N 3.07; Found: C 68.88; H 7.33; N 3.12%.

From Compound A and propyl bromide

2(d) (E)-4-(2-(3-(1-methylpropoxy)-3-oxo-2-methyl-1-propenyl)phenyl)-1,4-dihydro-2,6-dimethyl-3,5-pyridinedicarboxylic acid diethyl ester M.p. 113°–115°

Microanalysis for $C_{27}H_{35}NO_6$ Requires C 69.06 H 7.51 N 2.98; Found: C 69.14 H 7.57 N 2.99%.

From Compound A and sec-butyl bromide stirring for 10 h at 45°.

2(e) (E)-4-(2-(3-Octyloxy-3-oxo-2-methyl-1-propenyl)phenyl)-1,4-dihydro-2,6-dimethyl-3,5-pyridinedicarboxylic acid diethyl ester T.l.c. (methylene chloride/acetone, 100:15) Rf 0.52

Microanalysis for $C_{31}H_{43}NO_6$ Requires C 70.83; H 8.24; N 2.66; Found: C 70.55; H 8.28; N 2.60%.

From Compound A and octyl bromide.

2(f) (E)-(+S)-4-(2-(3-(1-Methylpropoxy)-3-oxo-2-methyl-1-propenyl)phenyl)-1,4-dihydro-2,6-dimethyl-3,5-pyridinedicarboxylic acid diethyl ester M.p. 128°–130°

$(\alpha)_D 20 = 19.5°$ (CH$_3$OH)

Microanalysis for $C_{27}H_{35}NO_6$ Requires C 69.06; H 7.51; N 2.98; Found: C 69.01; H 7.60; N 2.99%.

From Compound A and (−R) sec-butylmethanesulphonate stirring for 2 h at 55°.

2(g) (E)-(−R)-4-(2-(3-(1-Methylpropoxy)-3-oxo-2-methyl-1-propenyl)phenyl)-1,4-dihydro-2,6-dimethyl-3,5-pyridinecarboxylic acid diethyl ester M.p. 126°–128°

$(\alpha)_D 20 = -18.1°$ (CH$_3$OH)

Microanalysis for $C_{27}H_{35}NO_6$ Requires C 69.06; H 7.51; N 2.98; Found: C 68.98; H 7.58; N 2.98%.

From Compound A and (+S) sec-butylmethanesulphonate stirring for 2 h at 55°.

2(h) (E)-4-(2-(3-Pentyloxy-3-oxo-2-methyl-1-propenyl)phenyl)-1,4-dihydro-2,6-dimethyl-3,5-pyridinecarboxylic acid diethyl ester M.p. 126°–127°, t.l.c. (ethylacetate/petrol/ethanol 6:4:0.6) Rf 0.65

From Compound A and 1-bromopentane

2(i) E-4-(2-(3-Pentyloxy-3-oxo-2-ethyl-(propenyl)-phenyl)-1,4-dihydro-2,6-dimethyl-3,5-pyridinedicarboxylic acid diethyl ester as an oil, t.l.c. (cyclohexane/ethyl acetate/methanol 5:5:1) Rf 0.64: microanalysis for $C_{29}H_{39}NO_6$ requires C 69.99, H 7.90, N 2.82 found C 69.80, H 7.95, N 2.80%.

From Compound B and 1-bromopentane.

EXAMPLE 3

(Z)-4-(2-(3-Ethoxy-3-oxo-2-bromo-1-propenyl)-phenyl)-1,4-dihydro-2,6-dimethyl-3,5-pyridinedicarboxylic acid, diethyl ester A solution of Intermediate 2 (5.5 g) in ethanol (50 ml) was cooled to −10° and then trifluoroacetic acid (4 ml) was added followed by a solution of 3-amino-2-butanoic acid, ethyl ester (12.3 g) in ethanol (50 ml). The mixture was stirred at −10° for 1 h, evaporated in vacuo and the residue taken up in ethyl acetate, washed with 10% HCl, then with water and dried over Na$_2$SO$_4$. Evaporation of the solvent gave an oil. Purification of the oil by column chromatography (gradient diethyl ether/petrol ether, 8:2→9:1) gave the title compound as a white solid (3.2 g). M.p. 137°. T.l.c. (petrol ether/ethyl acetate, 1:1) Rf 0.38 and the corresponding E isomer as a white solid (0.2 g). M.p. 82°–84° (dec.). T.l.c. (petrol ether/ethyl acetate, 1:1) Rf 0.45.

EXAMPLE 4

Pharmaceutical compositions

(a) TABLETS

| (I) | mg/tablet |
|---|---|
| Active ingredient | 1 |
| Polyvinylpyrrolidone (PVP) | 20 |
| Lactose B.P. | 127 |
| Magnesium stearate B.P. | 2 |
| Compression weight | 150 |

The drug is granulated by a solution of PVP in ethanol, blended with the excipients and compressed using punches to suit.

| (II) | mg/tablet |
|---|---|
| Active ingredient | 1 |
| Microcrystalline cellulose BPC | 40 |
| Lactose B.P. | 100 |
| Sodium carboxymethylcellulose | 8 |
| Magnesium stearate B.P. | 1 |
| Compression weight | 150 |

The drug is sieved through a suitable sieve, blended with the excipients and compressed using punches to suit.

Tablets of other strengths may be prepared by altering the compression weight and using punches to suit. The tablets may be film coated with suitable film forming materials, e.g. methyl cellulose, ethyl cellulose or hydroxypropylmethyl cellulose, using standard techniques. Alternatively the tablets may be sugar coated.

(b) SOFT GELATIN CAPSULES

| | mg/capsule |
|---|---|
| Active ingredient | 1 |
| Polyethylene glycol (PEG) 400 | 199 |
| Fill weight | 200 |

The drug is dissolved in PEG 400 with stirring and the mix is filled into soft gelatin capsules using a suitable filling machine. Other doses may be prepared by altering the fill weight and if necessary changing the capsule size to accommodate the change in fill weight.

In the above pharmaceutical examples the active ingredient refers to one or more compounds of the general formulae (I) but is preferably 4-(2-(3-(1,1-dimethylethoxy)-3-oxo-2-methyl-1-propenyl)phenyl)-1,4-dihydro-2,6-dimethyl-3,5-pyridinedicarboxylic acid diethyl ester and more especially the E isomer thereof.

We claim:

1. A compound of the formula (I)

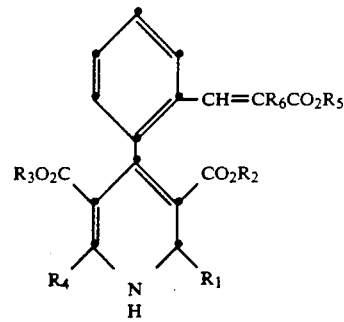

wherein
  $R_1$ and $R_4$ independently represent a $C_{1-4}$ alkyl group;
  $R_2$ and $R_3$ independently represent a $C_{1-6}$ straight or branched chain alkyl or alkoxyalkyl group;
  $R_5$ represents a $C_{1-13}$ straight or branched chain alkyl group or a $C_{5-8}$ cycloalkyl group which may be substituted by a $C_{1-3}$ alkyl group; and
  $R_6$ represents a halogen atom or a straight or branched $C_{1-3}$ alkyl group.

2. A compound as claimed in claim 1 in which $R_1$ and $R_4$ independently represent methyl or ethyl groups.

3. A compound as claimed in any of claim 1 in which $R_2$ and $R_3$ independently represent a $C_{1-4}$ alkyl or $C_{1-3}$ alkoxyethyl group.

4. A compound as claimed in claim 1 in which $R_2$ and $R_3$ independently represent groups selected from methyl, ethyl or isopropyl.

5. A compound as claimed in claim 1 in which $R_5$ represents a $C_{2-9}$ straight or branched chain alkyl group or a $C_{5-7}$ cycloalkyl group which may be substituted by $C_{1-3}$ alkyl.

6. A compound as claimed in claim 1 in which $R_5$ represents ethyl, propyl, secbutyl, tertiary butyl, pentyl, octyl or cyclohexyl.

7. A compound as claimed in claim 1 in which $R^6$ represents bromine, or a methyl or ethyl group.

8. A compound as claimed in claim 1 in which $R_6$ represents methyl or ethyl.

9. A compound as claimed in claim 1 in which $R_1$ and $R_4$ represent methyl, $R_2$ and $R_3$ independently represent methyl, ethyl, isopropyl, $R_5$ represents ethyl, propyl, secbutyl, tertiary butyl, pentyl or octyl or a cyclohexyl group and $R_6$ represents methyl or ethyl.

10. A compound as claimed in claim 1 in which $R_5$ represents a tertiary butyl group.

11. The compound, 4-(2-(3-(1,1-Dimethylethoxy)-3-oxo-2-methyl-1-propenyl)phenyl)-1,4-dihydro-2,6-dimethyl-3,5-pyridinedicarboxylic acid diethyl ester.

12. The compound selected from 4-(2-(3-(1-Methylpropoxy)-3-oxo-2-methyl-1-propenyl)phenyl)-1,4-dihydro-2,6-dimethyl-3,5-pyridinedicarboxylic acid diethyl ester;
    4-(2-(3-(cyclohexyloxy)-3-oxo-2-methyl-1-propenyl)-phenyl)-1,4-dihydro-2,6-dimethyl-3,5-pyridinedicarboxylic acid diethyl ester;
    4-(2-(3-ethoxy-3-oxo-2-ethyl-1-propenyl)phenyl)-1,4-dihydro-2,6-dimethyl-3,5-pyridinedicarboxylic acid diethyl ester.

13. The E isomer of the a compound as claimed in any of claim 1.

14. A compound as claimed in claim 1 in which $R_5$ represents a hydrogen atom.

15. A pharmaceutical composition comprising a compound as claimed in claim 1 in association with a pharmaceutically acceptable carrier or diluent.

16. A composition as claimed in claim 15 in a form suitable for oral, sub lingual, transdermal, parenteral or rectal administration.

17. Composition as claimed in claim 16 for oral administration in the form of a tablet or capsule.

18. Composition as claimed in claim 17 containing a dose of 0.01 to 50 mg of active ingredient.

* * * * *